United States Patent [19]

Geaghan

[11] 4,062,359
[45] Dec. 13, 1977

[54] LOW TEMPERATURE BREATHING APPARATUS

[76] Inventor: Mark E. Geaghan, 1910 Page St., No. 5, San Francisco, Calif. 94117

[21] Appl. No.: 712,490

[22] Filed: Aug. 9, 1976

[51] Int. Cl.² .......................................... A61M 15/00
[52] U.S. Cl. ................................................ 128/212
[58] Field of Search .............. 128/212, 208, 205, 202, 128/201, 192, 191 R, 140 R, 142 R, 145 R, 145 A, 146, 146.6, 146.3, 147

[56] References Cited

U.S. PATENT DOCUMENTS

| 2,317,237 | 4/1943 | Wilen | 128/145 A |
| 3,491,754 | 1/1970 | Weese | 128/212 |
| 3,707,966 | 1/1973 | Nebel | 128/212 |

FOREIGN PATENT DOCUMENTS

| 21,424 | 6/1882 | Switzerland | 128/212 |
| 27,118 of | 1896 | United Kingdom | 128/146 |

Primary Examiner—Robert W. Michell
Assistant Examiner—Henry J. Recla
Attorney, Agent, or Firm—Alfons Puishes

[57] ABSTRACT

A breathing apparatus for use by mountain climbers and others operating in low temperature atmospheres utilizes body heat and perspiration to warm and humidify the air from the atmosphere as it is inspired by the user. A hose-like element is positioned adjacent to the body and inside the clothing. The element is of a porous construction to permit passage of air and equipped with auxiliary holes for the same purpose. An inlet valve connects to the outer atmosphere and a filter and a connector lead to a face mask positioned against the nose and mouth of the user. An outlet check valve completes the apparatus.

4 Claims, 2 Drawing Figures

LOW TEMPERATURE BREATHING APPARATUS

BACKGROUND OF THE INVENTION

Operating in areas where the temperature of the atmosphere is in the sub-zero range produces several undesirable effects upon the human body. This is especially experienced by mountain climbers polar explorers, and others encountering similar environments. The first of these, of course, is loss of heat directly from the body surface and its attendant discomfort. The second is the inspiration of very cold dry air which has the combined effect of loss of body heat and difficulty in breathing. An added and related problem is the effect of inspiration of very dry air and consequent loss of moisture from the body which further aggravates the above conditions.

The manner in which body heat is lost has been studied by the Naval Medical Center at Bethesda, Md. and tabulated in the U.S. Navy Polar Manual as follows:
1. Direct loss from body surface — 63% to 70%
2. Evaporation of perspiration — 14% to 18%
3. Saturation of inspired air with water vapor — 8% to 9%
4. Warming of inspired air — 2% to 9%
5. Warming of ingested foods and fluids to body temperature — 1% or less.

By drawing inspired air from within the clothing, some heat loss directly from the body surface would be recaptured. When warm air is inspired instead of cold air, the heat loss occasioned by warming the latter is reduced. Air drawn from within the clothes also contains perspiration vapor which by purification through a simple filter can be made to retain a substantial part of its moisture, thus increasing its humidity and improving its breathing qualities. An added advantage is that in removal of the moisture in the clothes, the heat conduction is decreased and the insulating efficiency of the clothing improved, thus further decreasing the heat lost directly from the body surface.

Thus it is seen that not only warming of the inspired air would effect considerable saving in body heat but also elimination of the necessity for saturating the inspired dry air would have a like effect. What is produced in effect is a recycling of body moisture and the elimination of dehydration of the body.

The physiological effects of body chilling and dehydration are well known. They generally manifest themselves by a greater strain on the heart, increased blood pressure and pulse rates, increased urinary output often manifesting itself in headaches, indigestion, fatigue, and frost bite. These, in general, are the bad effects which recycling of the body heat and moisture as described herein, eliminates.

This problem has been recognized for some time as evident from the above reference. Several attempts have been made to solve it and the prior art, as known to the applicant at this time, is summed up briefly below.

U.S. Pat. No. 3,229,681 to Gluckstein utilizes a breathing or inhaling mask in combination with a chemical catalyst compartment which warms the air as it is being inspired.

U.S. Pat. No. 3,249,108 to Terman utilizes an electrical battery heated apparatus to warm the air on its way to the breather's mask.

U.S. Pat. No. 3,491,754 to Weese and U.S. Pat. No. 3,707,966 to Nebel both attempt to use body temperature in one way or another to heat incoming air. Weese uses a two layer pad with a simple tube leading to the mouth of the user. It necessitates heavy pressure against the chest, is rather bulky and provides no direct connection to the environment. Nebel employs a similar pad which has disadvantages similar to those of Weese. Both these devices are confined to only a small and localized area of the body and thus cannot possibly effect an efficient recycling operation as does the applicant. They cannot maintain close contact with the body which moves and angles considerably during climbing operations. Neither of these devices provide for moisture control.

SUMMARY OF THE INVENTION

I have invented what is believed to be a true device for effecting the equilibrium necessary to prevent excessive loss of body heat and at the same time provide good air for breathing when the user is exposed to a very cold environment.

My principal inlet element is a flexible hose made of porous material, such as fabric or woven plastic. I incorporate a helical reinforcing member throughout the length of my inlet element which retains the flexibility but at the same time gives it sufficient rigidity for close contact and urging against various parts of the body regardless of body position. I provide additional holes as desired in this element to increase the amount of intake air and combine this with the effect of an inlet valve which communicates between my inlet element and the outer atmosphere thus enabling me to blend the outer air with that inspired from under the garments to any extent that may be desired. The latter would depend on how cold the environment was and what the needs of comfort for the user were at the time.

My inlet element, of course, is located against the body and inside the outer garments. I provide also a filter connected in between my intake element and my face mask. The latter is positioned against the mouth and nose of the user and is equipped with an outlet check valve to the atmosphere.

My filter is made with a removable element which may be eleminated where inspiration of impurities from perspiration or other sources is not a problem. This would be especially true on relatively short hikes. The filtering material may be of any commercial type such as carbon or glass as desired and may be eliminated entirely when minimizing bulk is essential. In climbing to high altitudes the amount of equipment which it is necessary to pack makes it desirable to eliminate as much bulk as possible. This particular feature of my invention is another one which distinguishes it from the prior art.

DESCRIPTION OF A PREFERRED EMBODIMENT

Figure 1:
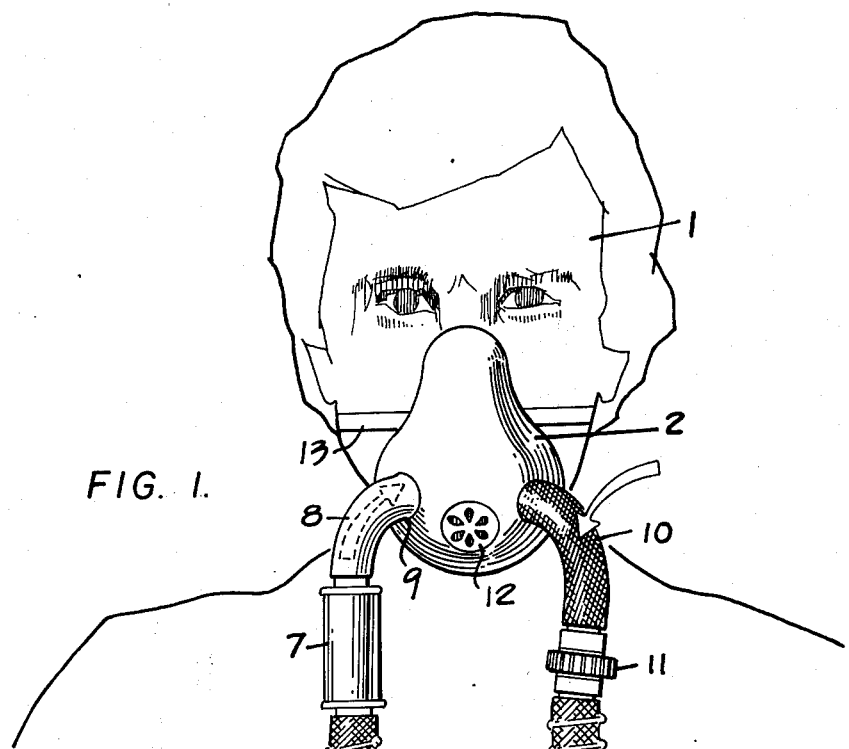
FIG. 1 shows the arrangement of my apparatus in position on the face of the user.

Referring now first to FIG. 1 there is seen diagrammatically the head of the user 1 with the mouthpiece 2 in position. The intake element 3 is essentially a hose-like member comprising a porous tube 4 combined with a helical reinforcing member 5, preferably positioned inside tube 4 and forming a part of it. The tube 4 may be made of fabric, woven plastic, or other porous material. The helical reinforcing member or spring 5 may be or any resilient material or metal which gives my element 3 a reasonable amount of rigidity and yet permits it to adapt itself closely to the surface of the user's body while the user is in motion. Actually, the net effect is that of a corrugated flexible hose, insofar as mechanical properties are concerned.

I may provide inlet holes 6 at various places along element 3 as needed to provide for easier admission of larger volumes of air. The cylindrical section 7 is a filter section in which I may position any desired type of filter medium such as charcoal or glass or other filter media, or I may dispense with the filter media, depending on the usage. The latter condition would be true in the case of short hikes or where perspiration is not a great problem. It may also be desirable to eliminate the filter medium in the interest of minimizing the bulk in the case of severe climbing expeditions. The inlet section 8 is a hollow member connecting to mouthpiece 2 at 9. A blind section of hose 10 supports the opposite end of element 3 upon the face mask 2 and is solid so that no air passes through it and is provided merely to hold the rest of the element in position.

The adjustable inlet valve 11 serves to admit air from the environment into my element 3 as needed. Its location with respect to the rest of the apparatus and user is best seen on FIG. 2.

The face mask 2 is equipped with a valving arrangement not shown which insures the inhalation of air through my element 3 only and exhalation through outlet 12. Fastening strip 13 serves to hold the mask 2 against the mouth and nose of the user.

Figure 2:
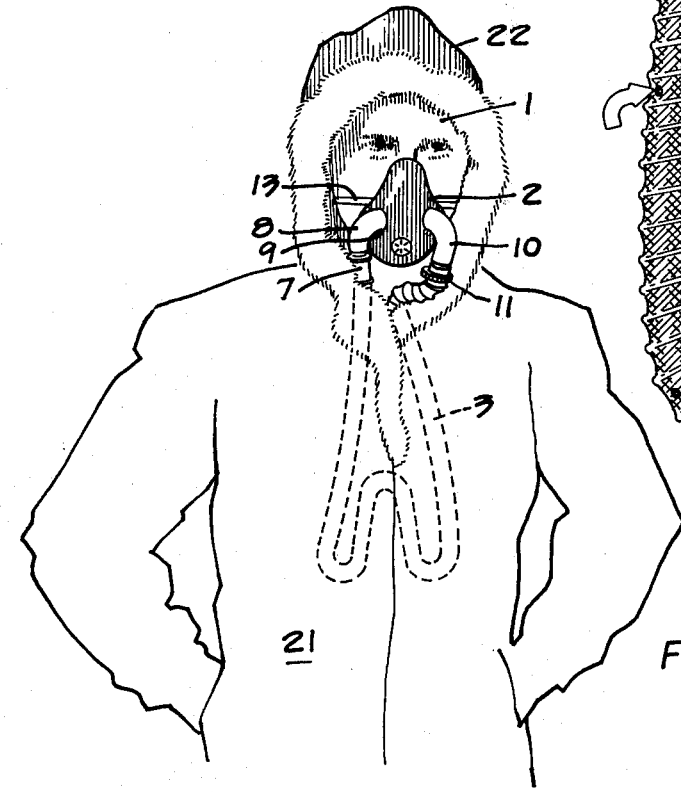
FIG. 2 is a partly schematic diagram showing my apparatus in relation to the user and his clothing.

On FIG. 2 there is shown the type of jacket or clothing 21 customarily worn by people in cold environments, together with a parka type of hood or head cover. This figure illustrates also the ease and flexibility which characterizes the application and use of my device as compared with others intended for the same purpose. It shows also the greater adaptability to a larger section of the body than other devices which have been tried for this purpose and have proved ineffective and inefficient.

I claim:

1. A breathing apparatus for inhalation of low temperature air by a person comprising:
   a tubular member having perforations linearly disposed therein and adapted for contact against said person's body inside his outer garments and having a first end and a second end;
   a face mask disposed for positioning against the nose and mouth of the user;
   a hollow tube positioned on said face mask and connecting the interior of said mask with said first end of said tubular member;
   a support member positioned on said face mask and connecting with said second end of said tubular member;
   valve means disposed to admit air from outside said outer garments to the interior of said tubular member;
   valve means to permit passage of air from the interior of said mask to the exterior only.

2. The apparatus of claim 1 including filter means inserted between said first end of said tubular member and said hollow tube.

3. The apparatus of claim 1 including spring means cooperating with said tubular member and disposed to impart a semi-rigid quality to said member.

4. The apparatus of claim 1 including holes through said tubular member positioned at spaced intervals along its length and disposed to increase the flow of air through said apparatus.

* * * * *